United States Patent [19]

Southgate

[11] Patent Number: 4,675,729
[45] Date of Patent: Jun. 23, 1987

[54] METHOD OF DETECTING BLEMISHES IN THE PHOSPHOR SCREEN ON A KINESCOPE FACEPLATE

[75] Inventor: Peter D. Southgate, Princeton, N.J.
[73] Assignee: RCA Corporation, Princeton, N.J.
[21] Appl. No.: 874,050
[22] Filed: Jun. 13, 1986
[51] Int. Cl.⁴ .............................................. H04N 7/18
[52] U.S. Cl. .................................... 358/106; 358/101
[58] Field of Search ................................ 358/106, 101

[56] References Cited

U.S. PATENT DOCUMENTS

| | | | |
|---|---|---|---|
| 4,454,541 | 6/1984 | Duschl | 358/106 |
| 4,454,545 | 6/1984 | Duschl | 358/213 |
| 4,542,404 | 9/1985 | Duschl | 358/106 |
| 4,575,751 | 3/1986 | Duschl | 358/106 |
| 4,605,960 | 8/1986 | Cohen | 358/106 |
| 4,625,237 | 11/1986 | Cohen | 358/106 |

Primary Examiner—Howard W. Britton
Attorney, Agent, or Firm—E. M. Whitacre; D. H. Irlbeck; L. L. Hallacher

[57] ABSTRACT

In a method of detecting blemishes in the phosphor screen on the inside surface of a kinescope faceplate while simultaneously avoiding detecting deposits on the outside surface of the faceplate as blemishes, the faceplate is arranged between a light source and a light detector in an orientation wherein light from the light source passes through the faceplate and subsequently through the phosphor screen prior to reaching the detector.

3 Claims, 4 Drawing Figures

METHOD OF DETECTING BLEMISHES IN THE PHOSPHOR SCREEN ON A KINESCOPE FACEPLATE

BACKGROUND

This invention relates generally to blemish detection and particularly to the detection of blemishes in the phosphor screen of a kinescope faceplate, or panel, while simultaneously avoiding the detection of deposits on the outside surface of faceplate as blemishes.

U.S. Pat. Nos. 4,454,541 and 4,454,545 describe various aspects of a system for detecting blemishes in various objects, such as the phosphor screens on kinescope faceplates. The inventions described in these patents are very satisfactory for most purposes. However, some difficulties have been encountered when they are utilized to detect blemishes in the phosphor screens on kinescope faceplates. Kinescope faceplates typically have a slightly curved viewing screen integral with substantially parallel sidewalls. The phosphor screens are formed by depositing stripes, or dots, on the concave inside surface of the faceplate. For a color kinescope, three different phosphors are applied, each of which emits a different color of light when impacted by electrons. Additionally, when viewed from the viewing or front side, the phosphor stripes, or dots, of which the screen is composed, are surrounded by a thin layer of black matrix material. When viewed from the screen side, the phosphors overlap the matrix material. The phosphors and the black matrix material are deposited by covering the entire internal surface of the faceplate with a photosensitive slurry containing the material to be deposited. An apertured shadow mask is inserted into the panel and the photosensitive slurry is exposed to light through the apertures. Because four different materials comprise the screen, a substantial amount of handling and processing is required during the formation of the screen. Additionally, the environment in which such processing takes place cannot be as clean as might be desired because of the inherent nature of the slurry application and the processing steps. For these reasons, there is a tendency for unwanted deposits, such as matrix material and phosphor splashes, or dust and dirt, to adhere to the outside surface of the faceplates.

After the screens are completely formed and a shadow mask is permanently inserted, the faceplates are permanently affixed to a funnel portion, and the final assembly steps are undertaken. A substantial number of parts are added during the final assembly and a substantial number of processing steps are required. For this reason, prior to mating a faceplate with a funnel portion, it is preferable to inspect the phosphor screens for blemishes, such as missing phosphor portions, or extra matrix material, so that screens having such blemishes are identified early in the processing stage to avoid the substantial expense of mating unusable faceplates with funnels. The inventions described in U.S Pat. Nos. 4,454,541 and 4,454,545 are used to inspect faceplates for blemishes. Although the patents do not describe the details of the illumination of the faceplates, initially when inspecting screens for blemishes, the entire phosphor screen was illuminated with light which first passed through the phosphor screen, and then the panel glass prior to reaching a light detector mounted within a camera. This method of inspection is very satisfactory in detecting blemishes in the phosphor screens of clean faceplates. However, difficulties have arisen in detecting blemishes in the screens of dirty faceplates. Unwanted deposits which accumulate on the outside surface of the faceplates can be identified as blemishes and result in the rejection of an acceptable faceplate. Cleaning of the faceplates is not desirable because of the additional expense of the otherwise unnecessary cleaning. For this reason, there is a need for a method for detecting blemishes in the phosphor screen on one surface of a faceplate, or other transparent object, in the presence of deposits on the other surface of the object, while simultaneously avoiding identifying the deposits as blemishes. The present invention fulfills this long felt need.

A further requirement for a satisfactory blemish detector is that the contrast detected for a blemish of a given size should be substantially the same irrespective of the location of the blemish in the faceplate. When the screen is viewed through the glass, it is possible for a particular blemish to be detected with a contrast that varies with the position in the screen. Thus, missing phosphor can show a reduced contrast when the blemish is close to the sidewall. The present invention gives a method of avoiding this contrast variation.

SUMMARY

In a method of detecting blemishes in the phosphor screen on the inside surface of a kinescope faceplate while simultaneously avoiding detecting deposits on the outside surface of the panel as blemishes, the faceplate panel is arranged between a light source and a light detector in an orientation wherein light from the light source passes through the faceplate and subsequently through the phosphor screen prior to reaching the detector.

DETAILED DESCRIPTION

Figure 1:
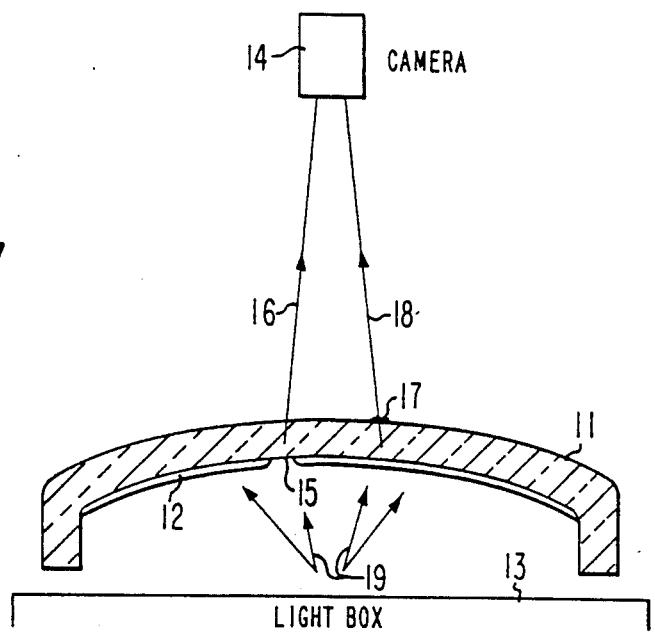
FIG. 1 is a sectional view showing how both blemishes in the phosphor screen, and dirt on the outside surface of a faceplate, are detected as blemishes when the illuminating light is placed on the phosphor side of the faceplate.

In FIG. 1, a kinescope faceplate 11 has a phosphor screen 12 on the inside surface. The panel 11 is supported between a light box 13 and a camera 14 whereby the phosphor screen 12 is illuminated by light rays 19 from the light box. The light box 13 emits diffuse light and the faceplate 11 is interposed in a direct line between the camera 14 and the light box. Light first passes through the phosphor screen 12 and then the glass faceplate 11, prior to reaching the camera 14. A lensing system within camera 14 causes the screen 12 to be focussed onto a detector, such as a charge coupled device (CCD). This focus may be adjusted to accommodate different sizes of panels, for which the distance between the faceplate 11 and the camera 14 may be varied. The screen 12 contains a blemish 15, so that the response of the portion of the detector receiving light from the blemish, along light path 16, is substantially different from the response of the portions of the detector which receive light from acceptable portions of the screen. Also, a small deposit 17 is adhered to the outside surface of the faceplate 11. This deposit is in direct view of the camera 14 along light path 18. The depth of field of the camera 14, when focused, is such that both the blemish 15 and the deposit 17 are clearly focused on the sensor within the camera. Accordingly, the detector portions receiving light rays 18 emanating from the deposit 17 also give a response which is substantially different from that of the portions receiving energy from the other portions of the screen 12. For this reason, the faceplate 11 would be rejected even in the absence of the blemish 15 within the screen 12. This is highly undesirable because the screen 12 is otherwise acceptable, and any deposits on the outside surface of the faceplate 11 are removed in a cleansing step later in the processing, after the faceplate is incorporated into a finished tube. The diffused light rays 19 from the light box 13 and the depth of field of the camera 14, thus, cause both blemishes in the screen 12 and deposits on the outside surface of the faceplate 11 to be focused on the camera 14 and result in the rejection of the panel 11.

Figure 2:
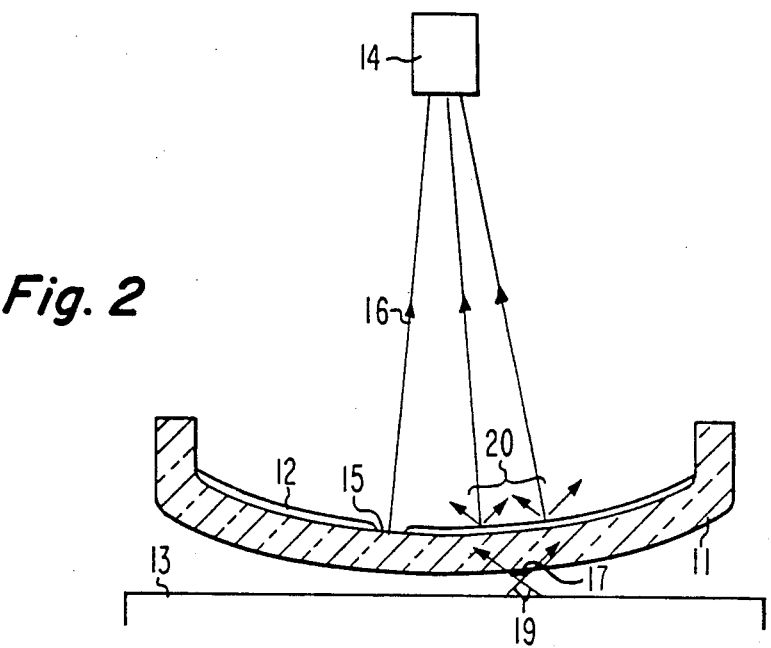
FIG. 2 is a sectional view showing how phosphor blemishes are detected, but deposits on the outside surface of the faceplate are not detected as blemishes, when the camera is placed on the phosphor side of the faceplate.

In FIG. 2, the faceplate 11 is oriented so that the diffused light rays 19 from the light box 13 pass through the panel 11 prior to reaching the phosphor screen 12 and the camera 14. In this arrangement the direct view of the deposit 17 from the camera is obscured by the screen 12. Accordingly, light rays 19 from the diffuse light source which pass in the vicinity of deposit 17 are scattered by the screen before they reach the camera. A diffuse shadow is therefore produced by the deposit 17 on screen 12 covering the approximate region 20 and it is this shadow that forms an image on the camera detector. Since the shadow covers a much larger area of the detector than did the original deposit viewed as in FIG. 1, the contrast is greatly reduced and the deposit is not detected as a blemish. The contrast of blemish 15 is of a similar magnitude to that given by the arrangement of FIG. 1. The screen 12 is seen by the camera 14 in transmitted light so that the sequence in which the light passes through the phosphor layer and the matrix openings has little effect on the final image. Accordingly, a faceplate containing the blemish 15 will be rejected. However, in the absence of a blemish, the faceplate is identified as an acceptable faceplate, even in the presence of a substantial number of deposits on the outside surface of the faceplate.

Tests have been conducted by placing dark crayon marks having sizes from 1 millimeter to 5 millimeters in diameter on the outside surface of the faceplate 11. Such marks produced no blemish indications when the camera 14 was placed on the phosphor screen 12 side of the panel 11, although blemishes in the phosphor screen were detected. Marks present on the outside surface of panels 11, which have a small fraction of the diameter of these test marks, result in rejections of panels when the camera 14 is placed on the viewing side of the panel 11.

Figure 3:
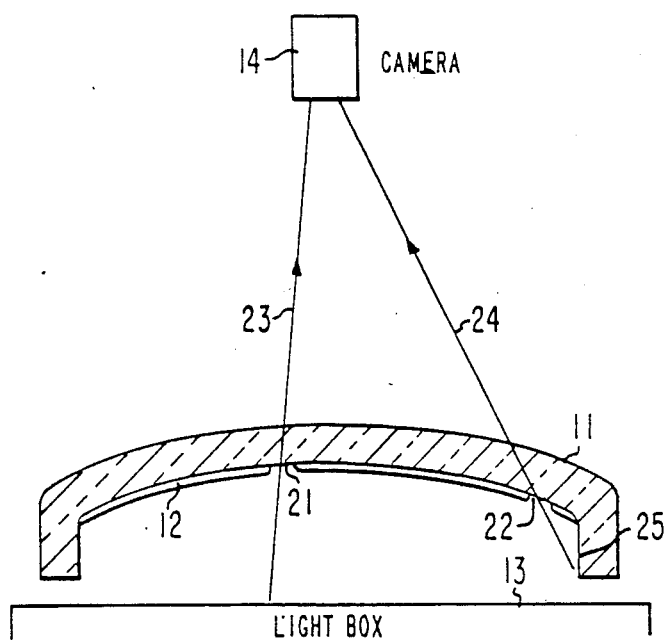
FIG. 3 is a sectional view showing how the detected brightness of two "missing phosphor" blemishes can vary with the location of the blemish when the faceplate is viewed from the glass side.
Figure 4:
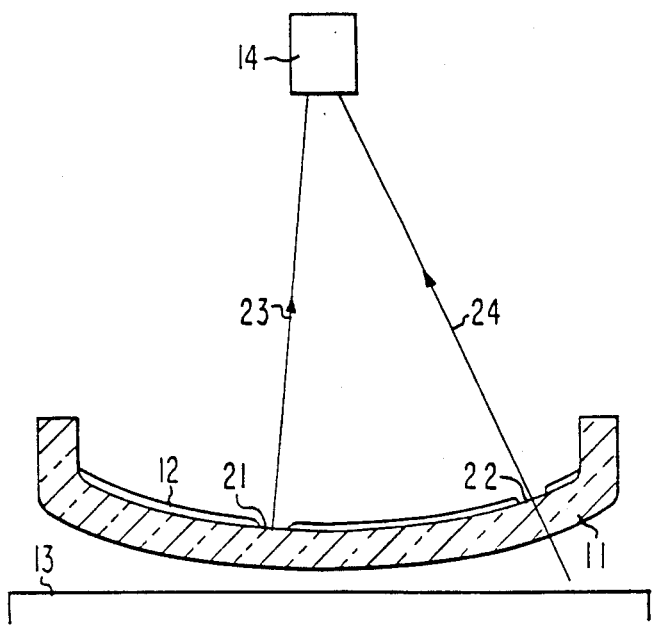
FIG. 4 is a sectional view showing how the detected brightness of the two blemishes of FIG. 3 is substantially constant for all screen locations when the screen is viewed from the phosphor side.

FIG. 3 shows another disadvantage of illuminating the faceplate 11 from the phosphor screen side. A blemish 21 is a "missing phosphor" type of blemish and the brightness on the camera detector corresponds to the brightness of the light box 13 viewed through the clear glass of the blemish along the light path 23. Another blemish 22 is of the same type and size as blemish 21, but is located near the sidewall 25 of the faceplate 11. Accordingly, the brightness corresponds to that of the sidewall 25 because the camera 14 sees the sidewall 25 through the blemish 22 along light path 24. The sidewall 25, typically, will have a substantially different brightness from the light box because the sidewall commonly is covered with black matrix material. The response of the camera detector to the two identical blemishes 21 and 22 can therefore be very different in the configuration of FIG. 3. In comparison, FIG. 4 shows the same two blemishes viewed from the phosphor side of the screen. Here, the light paths 22 and 23 both give views through the clear glass of the blemishes which reveal the light box surface. The blemish areas, as imaged on the camera detector, will therefore both have similar brightnesses, as is desirable if both blemishes are to be assigned a similar significance.

What is claimed is:

1. A method of detecting blemishes in the phosphor screen on the inside surface of a kinescope faceplate while simultaneously avoiding detecting deposits on the outside surface of said faceplate as blemishes and also avoiding changes in sensitivity to blemishes near the faceplate edge comprising the steps of:

arranging said faceplate panel between a light source and a light detector in an orientation wherein light from said light source first passes through said faceplate and subsequently passes through said phosphor screen prior to reaching said detector.

2. The method of claim 1 further including the step of passing light from said phosphor screen onto a CCD detector contained within a camera whereby the entire phosphor screen is focused onto said CCD.

3. The method of claim 2 further including the step of illuminating said faceplate with a light box which provides a substantially diffuse light field.

* * * * *